United States Patent
Puska et al.

(10) Patent No.: US 9,078,954 B2
(45) Date of Patent: Jul. 14, 2015

(54) MULTIFUNCTIONAL FILLER GRANULE

(71) Applicant: Pobi Concept Oy, Turku (FI)

(72) Inventors: Mervi Puska, Turku (FI); Allan Aho, Turku (FI); Pekka Vallittu, Kuusisto (FI)

(73) Assignee: POBI CONCEPT OY, Turku (FI)

( * ) Notice: Subject to any disclaimer, the term of this patent is extended or adjusted under 35 U.S.C. 154(b) by 0 days.

(21) Appl. No.: 13/764,175

(22) Filed: Feb. 11, 2013

(65) Prior Publication Data

US 2013/0230563 A1 Sep. 5, 2013

(30) Foreign Application Priority Data

Mar. 2, 2012 (EP) ..................................... 12157817

(51) Int. Cl.
*A61L 27/40* (2006.01)
*C08J 5/04* (2006.01)
(52) U.S. Cl.
CPC ... *A61L 27/40* (2013.01); *C08J 5/04* (2013.01)
(58) Field of Classification Search
CPC ....... C08F 20/14; C08F 2/44; H04B 10/2513; H04B 10/677
See application file for complete search history.

(56) References Cited

U.S. PATENT DOCUMENTS

| 3,780,156 | A | * | 12/1973 | Cameron | ....................... | 264/300 |
| 5,169,710 | A |  | 12/1992 | Qureshi et al. | | |
| 5,336,699 | A | * | 8/1994 | Cooke et al. | .................. | 523/115 |
| 2007/0054244 | A1 | * | 3/2007 | Vallittu et al. | ............. | 433/217.1 |
| 2009/0258965 | A1 | * | 10/2009 | Lassila et al. | ................. | 523/116 |

FOREIGN PATENT DOCUMENTS

| EP | 0696629 | 2/1996 |
| WO | 02074356 | 9/2002 |

* cited by examiner

*Primary Examiner* — Audrea Buckley
(74) *Attorney, Agent, or Firm* — Tarolli, Sundheim, Covell & Tummino LLP

(57) ABSTRACT

The invention relates to a filler granule comprising a matrix component (1), at least two base particles (2) that are at least mostly embedded in the matrix component, and a fibrous component (3). The fibrous component is attached to at least one of the base particles. The invention also relates to uses of these filler granules as well as to composite materials containing them.

12 Claims, 3 Drawing Sheets

MULTIFUNCTIONAL FILLER GRANULE

FIELD OF THE INVENTION

The present invention relates to a filler granule comprising a matrix component, at least two base particles that are at least mostly embedded in the matrix component, and a fibrous component. The invention also relates to a method for manufacturing said filler granule as well as its uses.

BACKGROUND OF THE INVENTION

Different resorbable materials have been used for the treatment of tissue defects in medicine, with the use of synthetic organic and inorganic materials increasing in the past years. Their advantages are that large amounts of these materials can be rapidly produced, their properties can be tailored according to the clinical requirements and there is no or at least considerably less unwanted immunological reactions compared to autologous tissue transplants.

Several biodegradable polymeric materials have been developed for medical applications. Most materials are polyester derivates, of which polylactide and caprolactone are best documented. These polymers are currently considered as biocompatible, non-toxic materials. Certain polyester copolymers ($\epsilon$-caprolactone-D, L-lactide) can remain mouldable in low temperatures, which make it possible to inject them into tissue defects as disclosed in WO 99/022011 (Aho et al.).

Also several composites comprising polymer(s) are designed for medical applications in order to improve the contact between the living tissue and the composite. The connection between the composite and the living tissue is normally only mechanical, because the structure of the composite is usually too dense after implantation and does not allow any place for new tissue ingrowth inside the composite material. Therefore, the contact area between the composite and the living tissue is only limited to the contact surface between them. A porous material would solve this problem by providing a larger contact area between the tissue and the material.

Document WO 2002/074356 discloses one possible composite material for use for attaching, growing and repairing of living tissues. The composite comprises a non-expandable matrix polymer and a water-expandable porosity agent. The composite thus comprises a component that, once in contact with body fluids, expands (swells) and breaks the originally continuous phase of the matrix thus exposing the expanded component to the body fluids and reveals the bioactive part of the composite. The voids formed in the composite thereby come into contact with the surrounding tissue.

There remains however still a need to provide an improved material for use as a filler granule in composite materials.

OBJECTS AND SUMMARY OF THE INVENTION

It is therefore an object of the present invention to provide a material that can be used as a filler granule in various composite materials. The filler granule (hereinafter also referred to as granule) is designed to improve the porosity of the final composite material and/or to improve the bonding of the different phases of the final composite material to each other.

The filler granule, its manufacturing method and uses are as described in the independent claims hereinafter. The dependent claims define some advantageous embodiments of the invention.

A typical filler granule according to the present invention comprises a matrix component, at least two base particles that are at least mostly embedded in the matrix component, and a fibrous component. It is characterised in that the fibrous component is attached to at least one of the base particles.

A typical method for manufacturing a filler granule according to the present invention comprises the steps of mixing the fibrous component and the at least two base particles in such conditions that the fibrous component is attached to at least one of the base particles, and mixing the thus obtained mixture with the matrix component or a precursor of the matrix component.

The filler granule according to the invention may be used in composite materials and/or in the manufacture of medical devices.

DEFINITIONS OF TERMS USED

Figure 1:
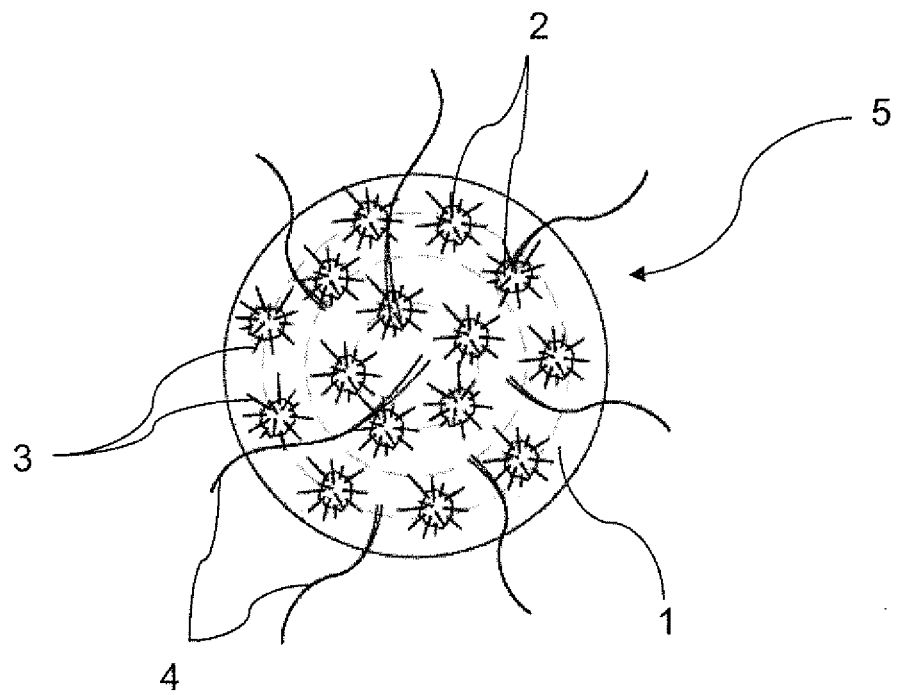
FIG. 1 schematically shows a filler granule according to an embodiment.

The terms used in this application, if not otherwise defined, are those agreed on at the consensus conference on biomaterials in 1987 and 1992, see Williams, D F (ed.): Definitions in biomaterials: Proceedings of a consensus conference of the European Society for Biomaterials, Chester, England. Mar. 3-5, 1986. Elsevier, Amsterdam 1987, and Williams D F, Black J, Doherty P J. Second consensus conference on definitions in biomaterials. In: Doherty P J, Williams R L, Williams D F, Lee A J (eds). Biomaterial-Tissue Interfaces. Amsterdam: Elsevier, 1992. In this application, by bioactive material is meant a material that has been designed to elicit or modulate biological activity. A biodegradable material is a material that breaks down in vivo, but with no proof of its elimination from body.

The term bioresorbable in this context means that the material is disintegrated, i.e. decomposed, upon prolonged implantation when inserted into mammalian (or other animal/species) body and when it comes into contact with a physiological environment. The by-products of a bioresorbable material are eliminated through natural pathways either because of simple filtration or after their metabolization. The terms bioresorbable and resorbable can be used interchangeably, but is it is clear that bioresorption is meant in this description. By the term bioabsorbable it is meant a material that can dissolve in body fluids without any molecular degradation, and then excreted from the body.

By biomaterial is meant a material intended to interface with biological systems to evaluate, treat, augment or replace any tissue, organ or function of the body. By biocompatibility is meant the ability of a material used in a medical device to perform safely and adequately by causing an appropriate host response in a specific location, causing no foreign-body reactions and being non-toxic.

In this application, by curing it is meant polymerisation and/or cross-linking. By matrix, it is understood the continuous phase of the composition and by uncured matrix it is meant a matrix that is in its deformable state but that can be cured, i.e. hardened, to a non-deformable state. The uncured matrix may already comprise some long chains but it is essentially not yet polymerised and/or cross-linked. By partially uncured it is meant that the material is partly cured but still contains short chains that can be polymerised and/or cross-linked, and that the material is still in a deformable state. By composite is meant a material comprising at least two different constituents.

In the present context the term medical devices relates to any kind of implant used within the body, as well as devices used for supporting tissue or bone healing or regeneration. An implant according to the present context comprises any kind of implant used for surgical musculoskeletal applications such as screws, plates, pins, tacks or nails for the fixation of bone fractures and/or osteotomies to immobilize the bone fragments for healing; suture anchors, tacks, screws, bolts, nails, clamps, stents and other devices for soft tissue-to-bone, soft tissue-into-bone and soft tissue-to-soft tissue fixation; as well as devices used for supporting tissue or bone healing or regeneration; or cervical wedges and lumbar cages and plates and screws for vertebral fusion and other operations in spinal surgery. "Dental restoration" is used as meaning typical dental fillings but also as a general term to include all dental repairs, such as crowns and bridges. By body is meant a body of any animal including mammals such as humans, household animals, pets such as dogs and cats etc.

By the term fiber in this application is typically meant a fiber having a diameter in the micrometer range, i.e. up from 1 µm. By the term fibril, is typically meant a fiber-like object which diameter is smaller than 1 µm. The term fiber can however sometimes be used to designate also fibers which have a diameter of less than 1 µm. By the term hybrid material is typically meant a material that is a combination of both organic and inorganic material.

DETAILED DESCRIPTION OF THE INVENTION

A typical filler granule according to the present invention thus comprises a matrix component, at least two base particles that are at least mostly embedded in the matrix component, and a fibrous component. It is characterised in that the fibrous component is attached to at least one of the base particles.

The filler granule according to the invention is in fact a composite material itself and can be also called a multifunctional composite filler. Indeed, the base particles in the filler granule strengthen the structure of the granule. The structure of the granule is further strengthened by the fibrous component that is attached to at least a part of the base particles. The attachment of the fibrous component to the base particles can be either chemical or mechanical.

There are typically more than two base particles, such as from 5, 10, 15, 20, 30, 40, 50 or 60 base particles up to 30, 40, 50, 60, 70, 80, 90, 100, 150, 200, 250 or more base particles. The amount of base particles is selected according to the intended use of the filler granule. Their amount is only mentioned here to stress the fact that the fibrous component does not need to be attached to each single base particle. Preferably, the fibrous component is attached to at least 50% of the base particles, especially preferably to more than 50%, more than 60%, more than 70%, more than 80%, more than 85%, more than 90% or more than 95% of the base particles. It can naturally be attached to essentially all of the base particles and this is typically the most preferred solution.

The main object of the invention is thus to make filler granules that can be used for short- or long-term improvement of attachment of the fillers to the matrix while at the same time reinforcing the final material. By final material or final composite or final product is here meant the material in which the filler granules are used.

A part of the fibrous component protrudes out from the matrix component. In medical as well as in other applications, the protruding fibres improve the bonding of the two components (fillers and matrix) together. The protruding fibres have the further advantage of guiding tissue ingrowth when used in medical applications.

In these particular filler granules, the fibres thus improve the structural strength of the filler granules themselves as well as the structural strength of the composite material comprising the filler granules. The function of these filler granules is therefore to reinforce composite material by connecting and/or protruding fibres. These enable initial and/or long-term attachment of the fillers to matrix of the final composite material by reinforcing the interface between the fillers and the matrix.

The filler granules according to this invention can be resorbable, partially resorbable or non-resorbable. In tissue engineering, the fibres of the filler granules increase its attachment to the matrix and/or biological systems. Once the fillers have been partially dissolved, absorbed, removed or resorbed, the connecting fibres at the interface layer remain. These protruding fibres also allow tissue ingrowth into the porous structure.

The filler granule can also have a structure of active gradient, i.e. the filler can have several active layers. These layers can be of a same or different materials. They can be amorphous, partly crystallised or fully crystallised structures or they can differ from each other by their dissolution rate or composition. An active gradient filler can be manufactured for example by vapour drying technique or by dipping the fillers in one or more different solutions. The solutions can also comprise mixtures of several monomers.

According to another embodiment, the size of the filler granule is 5 nm-200 µm. The size of the filler granule can for example be from 5, 10, 15, 25, 50, 75, 100, 200, 500, 750, 1000, 1500, 2000, 5000 nm or 10, 25, 50, 75, 100, 150 or 175 µm up to 10, 15, 25, 50, 75, 100, 200, 500, 750, 1000, 1500, 2000, 5000 nm or 10, 25, 50, 75, 100, 150, 175 or 200 µm. A mixture of filler granules of different sizes can naturally be used, depending on the intended final use.

According to an embodiment, the surface of the filler granules can be modified in a manner that assists the activation of interfaces at any structural level, in the final composite material comprising the filler granules. The modification may be such that the activation can be induced by external moisture (e.g. body fluids) and/or energy (e.g. ultra sound, heating, magnetic treatment). In terms of moisture, the function of the interface activation within the interfaces can be to cause the porosity development, with an aim to produce a fully porous structure with totally interconnected pores or a porous structure only on the outermost surfaces. Additionally, the activation of interfaces also can increase the delivery of any chemical or biological substances, compounds or components from the composite or into it. In the leaching and/or activation, functionally active systems can be isolated from nature, produced synthetically or by means of molecular biology.

The surface of the filler granules can also be modified during their manufacture or at a later stage. The filler granules may also contain materials that can be activated once the finished material containing the filler granules is incorporated to the body. Surface treatment or modification may be useful in order to enhance the chemical and/or biological compatibility of the filler granule with the matrix material of the finished composite.

As mentioned above, one special advantage of the filler granules is that they can induce a porous interface between the composite wherein they are contained and the surrounding environment. For example, this can be the interface between bone and an implant. Porosity of this interface enhances the bone ingrowth and sufficient osseointegration. The tissue (bone, soft tissue, etc.) ingrowth can be desirable either only on the surface parts of the material or within its whole depth. The structure of poly(dimethyl)methacrylate (PMMA) and other polymer-based bone cements is as such not sufficient porous for an ideal effect in these applications, as it is typically less than 5 vol-%. They further have the disadvantage that during hardening of the bone cement, too dense surfaces are formed, thus hindering the attachment and ingrowth of the bone tissues to the implant or prostheses and leading to potential problems of detachment of the prostheses. Indeed, poor attachment allows the prostheses to move a few millimeters with respect to the surrounding bone, when the patient moves. This then leads to detachment and a need for a new operation.

The porosity can be created using filler granules according to this invention as so called pore-generating fillers or porogens, that are hydrophilic or hydrolytically degradable and/or enzymatically degradable. Alternatively, porogens can be designed to be degradable under ultrasonic, magnetic, thermal or radiant energy. The degradable substance can be either the filler granule in its entirety or a part of the filler granule, for example its base particles and/or fibrous component.

Thus the porogen can be in the shape of any kind of particle, like fibres, fibrils, spheres or granules. When the porogen is only a part of the present filler granule, it contains also co-filling components. The role of these co-filling components is both to reinforce and increase the attachment between the matrix of the final product and the filler granules at all scales (macro, micro and nano levels). In biological systems, the role of the co-filling components can also be to increase interconnective porosity formation and tissue guiding. According to one embodiment, the porous structure, once the pore formation is finished, becomes a bioactive surface with strand structure, which guides the tissue growth.

Totally or partly degradable filler granules are thus the structural components that enable to tailor-make the mechanical properties and increase the porosity formation. In order to be functionally active, the co-components of the filler granules or their functional groups can be such that they are activated by some outer stimulus or chemical interaction or reaction. This can be a hydrolytical reaction with body fluids or with some functional groups in the matrix of the final product. Alternatively, the outer stimulus also can be ultrasonic, magnetic, thermal or radiant energy or a combination thereof.

In terms of interfacial interactions, the filler granules play a key role. In the case of porogens, the porosity formation capacity will be optimised by tailor-making chemical interaction between co-fillers and matrix of the filler granule, thus leading to biologically active porous structures in the final composite.

Suitable materials are essentially any materials that can be manufactured in the desired form and that are suitable as such for the intended final composite material use. In biological applications, the biocompatibility is naturally an essential requirement for the materials. The filler granules may consist of one single material, of two different materials, of three different materials, or of more than three different materials.

The filler granule may be resorbable, partly resorbable or non-resorbable, depending on the intended end use.

Some examples of suitable materials are glasses such as biologically inert E-glass or a bioactive and/or biodegradable glass, other ceramic materials such as sol-gel derived materials, various polymers (both synthetic and natural) or combinations and/or hybrids of materials. The materials can thus be natural or synthetic and may for example be manufactured by molecular biology processes. The filler granule may also comprise monomers, oligomers, resins, homopolymers, copolymers, polymer blends, ceramics, metals or biological materials. Some examples of suitable materials are calcium phosphates, calcium sulphates, metal oxides (such as titanium dioxide, silicon dioxide) and collagen.

According to one embodiment of the invention, the matrix is made of a material selected from the group consisting of polylactides, polycaprolactones, polydimethylmethacrylates, polyamides, polyesters of aminoacids, bisphenol-A glycidyl methacrylate, polyvinyl acetates, carboxy methyl celluloses, L-4-hydroxyproline ethylester, polyamide of L-4-hydroxyproline and mixtures thereof.

According to another embodiment of the invention, the base particles are made of a material selected from the group consisting of polylactides, polycaprolactones, polydimethylmethacrylates, polyamides, polyesters of aminoacids, bisphenol A glycidyl methacrylate, polyvinyl acetates, carboxy methyl celluloses and mixtures thereof. The matrix and the base particles may be made of different or the same material, different materials being however preferred.

According to yet another embodiment of the invention, the fibrous component is made of a material selected from the group consisting of E-glass, bioactive glasses, sol-gel derived materials, and mixtures thereof.

Some more suitable specific materials are disclosed below in the Experimental section.

The fibrous component can be manufactured by electrospinning or traditional fibre drawing methods. A suitable diameter of the fibres or fibrils is 1 nm-100 µm. The fibrous component is then mixed with the base particles and attached at least partly to the surfaces of the base particles. Electrospinning can be used to make a mesh, i.e. a network of fibers made for example of fibers chopped to a specific length.

According to an embodiment, the fibrous component is formed of fibres in the form of short fibres, continuous fibres, a fibre mat or a fibre web. The fibrous component may also be in the form of a fibre grid, or any other suitable form. According to another embodiment, the diameter of the fibres is 1 nm-100 µm.

The filler granule may further comprise groups that degrade hydrolytically and/or enzymatically. Such groups can include structures or groups such as polysaccharides, carbohydrates, inorganic salts, dissolvable glass or metal compounds, dissolvable silicon dioxide compounds, amino acids, amino acid derivatives, polyamides, polyesters, compounds modified with a halogen or phosphorus, (meth)acrylate monomers or synthetic or natural biodegradable polymers.

The amino acid derivatives can be one single compound or a mixture of two, three or more compounds. They may be for example polyamides or polyesters of amino acids, or their amine group and/or carboxylic acid groups can be functionalised by an acryl or an (meth)acryl group, an epoxide or (poly)phosphazene. Their structures can be linear or partly or fully cross-linked. In case of cross-linking, the bonds can be covalent bonds, ionic bonds, hydrogen bonds or van der Waals bonds.

The matrix of the filler granule may in some applications comprise at least one functionality that can be activated with external energy, hydrolysis and/or enzymatically. The external energy can be selected from the group consisting of ultrasound, light (UV, visible, laser) or magnetic energy. This way, the material can be activated once it has been implanted. For example, an implant material may first be left to heal with the surrounding tissue and after a certain time (for example a few weeks or months), it can be activated to induce its biodegradation.

According to an embodiment, the filler granule further comprises at least one additive. According to another embodiment, the additive is selected from the group consisting of antibacterial agents, surface active agents, X-ray opaque agents, other therapeutically active agents, viruses, growth factors, stem cells, magnetically active or activated agents, light-activated agents, ultrasound-activated agents, polymerisation initiators and mixtures thereof.

According to a yet further embodiment, the filler granule comprises further reinforcing particles and/or fibres. These reinforcing particles and/or fibres would then be essentially unattached to the base particles.

As has been discussed above, the function of the filler granule can be
to enhance the dissolution of a porogen
to fixate a porogen to the matrix
to fixate a polymer powder of a bone cement into the matrix
to guide tissue growth
to enhance bone formation and attachment to tissue (bone and/or soft tissue)
to reinforce the structure of the finished product
to improve the antimicrobial properties
to enhance the bioactive properties
to function as a carrier and release controlling agent for therapeutically active agent, a growth factor, stem cells and/or other cells.

The present invention also relates to a method for manufacturing a filler granule comprising
a matrix component,
at least two base particles that are at least mostly embedded in the matrix component, and
a fibrous component,
the method comprising the steps of
mixing the fibrous component and the at least two base particles in such conditions that the fibrous component is attached to at least one of the base particles, and
mixing the thus obtained mixture with the matrix component or a precursor of the matrix component.

According to an embodiment of the invention, when a precursor of the matrix component is used, the method further comprises the curing of the precursor. The precursor thus means for example a monomer or an oligomer or a cross-linkable polymer, thus curing meaning either polymerisation or cross-linking. The matrix may also be a material that is then sintered (i.e. cured). According to one embodiment, the filler granule is formed when the matrix material is polymerised.

According to another embodiment, the method may also comprise a coating step. During the coating step, a new layer is formed in the structure or on its outermost layer. The layer may be for example made of polymer. The thickness of such layer can be for example from 1 nm to 1 µm. The coating may be made for example by dipping or spraying, and the dipping solution or spray can further contain one or more other functionally active agents such as a therapeutically active agent, a biological polymer or an antibacterial agent.

A fully or partly biodegradable composite filler can be manufactured by light or ultrasound polymerisation in a dilute solution. The core of such composite filler can have the form of a particle, a sphere, a fibre or a granule. The core can be coated in a liquid containing monomer of the coating polymer. The monomer is then attached fully or partly onto the surface of the core when polymerisation occurs.

The present invention yet further relates to the use of a filler granule in composite materials. The composite materials may be for wood industry, construction industry and/or plastics industry. A more specific example of suitable use is in antimicrobial materials, such as for moist environments. Some suitable uses for the filler granules are for example as filler particles in various plastic materials, such as biodegradable plastics that are used for manufacturing biodegradable plastic bags, disposable dishes, etc. The filler granules according to the present invention can also be used in wood industry, such as for manufacturing chipboard, in order to increase its strength. They can also be used in adhesives such as composite glues.

The filler granules according to the present invention can be used in conventional composites or in combination with modified matrix materials. When modified matrix materials are used, the affinities of the modifications are preferably as advantageous as possible for hydrolytical and/or enzymatical degradation. In these cases, the hydrolysis and/or enzymatic degradation is induced by body fluids and enzymes present in the implantation site.

The filler granules may thus be used in various composite materials to improve internal adhesion of the components to each other and/or to improve external adhesion of the filler granules to surrounding environment. They may further be used for creating porosity inside a bulk material.

According to another embodiment, the filler granules can be used in the manufacture of medical devices. The medical device may be selected from the group consisting of implants, dental restoration materials, dental bridges, dental prostheses, bone substitute materials, bone cements and combinations thereof.

The invention thus relates to a material that can be used for replacement of biological tissue such as bone or soft tissue. In such applications, the materials are preferably at least partially biodegradable and even more preferably, contain materials with different biodegradation rates. A material for replacement of biological tissue can be for example a bone substitute material or a bone cement. These materials can be plastics, inorganic compounds (such as salts) or polymer-based composites. Most typically the plastic materials are polyolefins or acrylate-based polymers. A material suitable for restoring a tissue damage can be for example poly(dimethyl)methacrylate (PMMA) or another acrylic polymer-based material containing filler granules according to this invention.

The matrix material can be also functionalised or grafted with groups that enhance the biodegradation of the filler granules. One example of functionalisation is to attach 10-30 mol-% of a sol-gel derived structure into the polymer backbone. An object for the functionalisation may be to enhance interphase diffusion, that in turn enhances porosity formation and improves affinities as well as delivery of active agents and absorption of the external energy.

These materials may also be used for example in the following applications: in the filling of cancellous bone defect as bone graft substitute, such as in the case of benign bone tumors (bone cysts, enchondromas); for defects caused by osteoporosis and bone fracture (such as spinal replacements or wrist fractures); in joint replacement surgeries as binding agents for the prostheses; replacement material for other tissues such as eyes or teeth; keratoprosthesis of an eye.

The present invention yet further relates to a composite material comprising at least one filler particle according to this invention. The amount of these filler particles can be for example 1-80 wt-% of the total weight of the composite, or 5-50 wt-%, 20-80 wt-%, 20-40 wt-% or 30-70 wt-%.

DETAILED DESCRIPTION OF THE DRAWING

FIG. 1 schematically shows a filler granule according to an embodiment. In this embodiment, the base particles 2 are embedded in a matrix component 1. The fibrous component 3 is attached to the base particles and protrudes out to the matrix component. There are further some reinforcing fibers 4 protruding from the filler granule. Together, these components form a first filler granule 5 according to the present invention.

Figure 2:
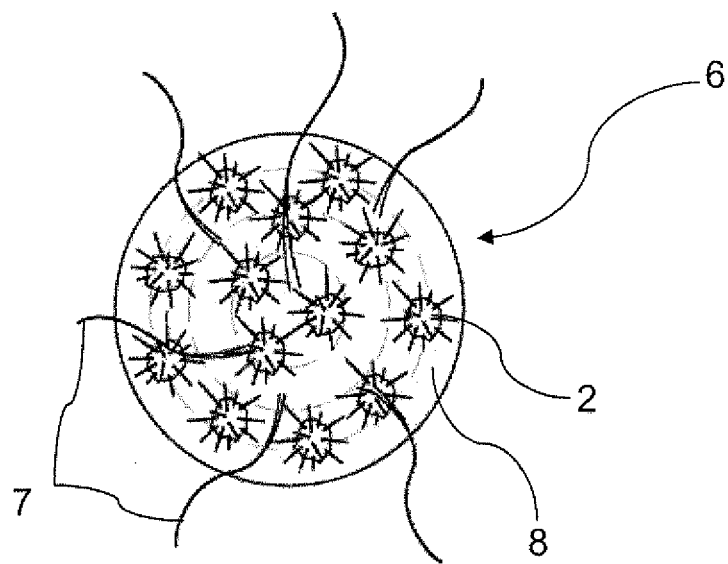
FIG. 2 schematically shows a filler granule according to another embodiment.

FIG. 2 schematically shows a filler granule according to another embodiment. In this Figure, filler granules as shown in FIG. 1 have been used to form a further composite filler granule, i.e. the granule 6 as shown in this Figure contains several filler granules 5 as shown in FIG. 1 as well as a second matrix component 8. The longer fibers 7 shown in FIG. 2 are partly reinforcing fibers and partly form a part of the fibrous component, and can be selected to be pore-forming fibers in medical applications, for example.

The enlargement used in FIG. 2 is thus smaller than the enlargement used in FIG. 1. Either the filler granule 5 or the filler granule 6 may further contain other components, such as therapeutically active agents, but these have been omitted from the Figures for sake of clarity.

Figure 3:
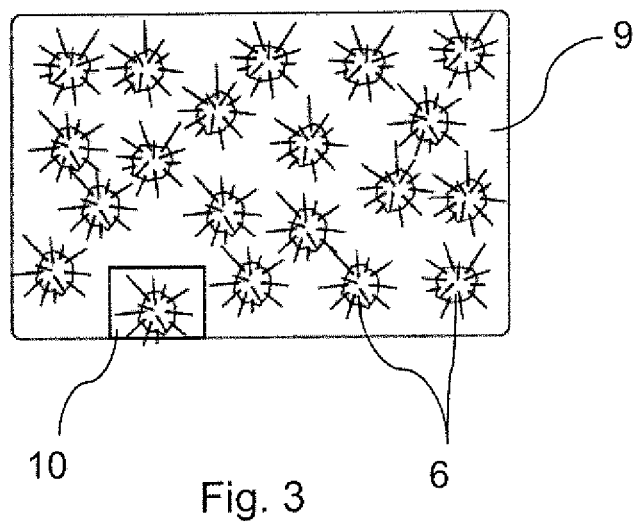
FIG. 3 schematically shows a composite material according to an embodiment.

FIG. 3 schematically shows a composite material according to an embodiment. The composite material contains filler granules 6 and a composite matrix 9. With reference number 10, a detail of the material is shown, the same detail will be shown in FIG. 4 below.

Figure 4:
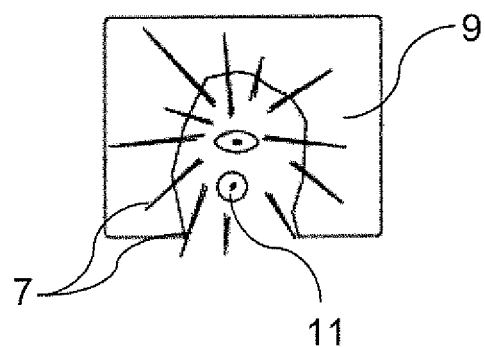
FIG. 4 schematically shows an enlargement of a part of the composite material shown in FIG. 1, after insertion to a body.

FIG. 4 schematically shows an enlargement of a part of the composite material shown in FIG. 1, after insertion to a body. This Figure shows how the filler granule 6 has degraded, leaving a void in the structure and fibers 7 protruding now from the void towards the remaining composite matrix 9. The void is starting to be filled with living cells 11.

Figure 5:
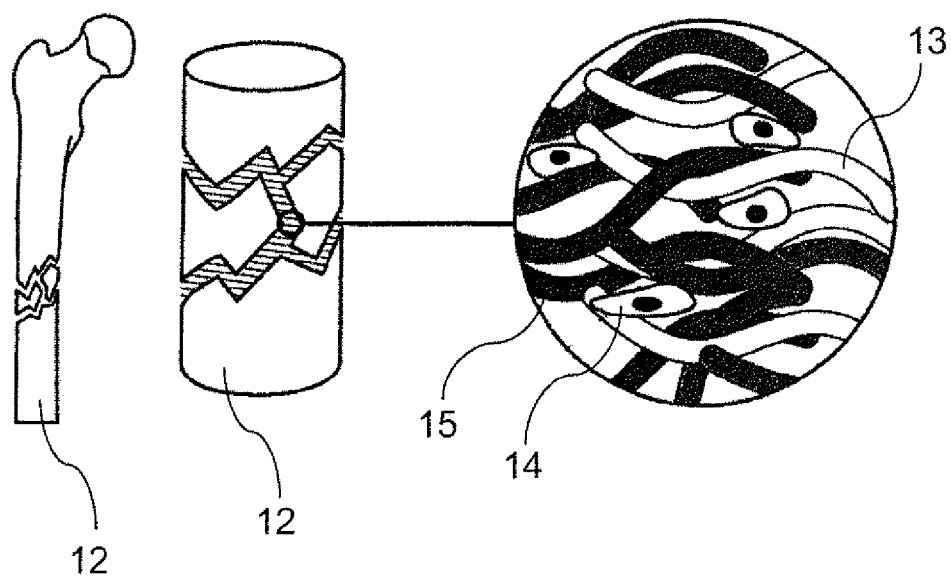
FIG. 5 schematically shows a bone fracture wherein a material according to an embodiment has been used.

FIG. 5 schematically shows a bone fracture wherein a material according to an embodiment has been used. On the left, a fractured bone 12 is shown. In the middle, the fracture is schematically shown as it as been filled with a composite bone cement comprising filler granules according to the present invention. In the right, the microstructure is shown, and it consists of the composite bone cement 13, cells 14 and collagen fibers 15, that have grown into the composite bone cement.

EXPERIMENTAL SECTION

In the following, wt-% means weight percentage and vol-% means volume percentage.

Example 1

Functionalisation of an Amino Acid with an Ethylester

An ester, such as an ethyl ester, is manufactured by acid catalysis from a carboxylic acid of an amino acid (100 mol-%, e.g. L-4-hydroxyproline). L-4-hydroxyproline ethylester hydrochloride salt is synthesised from L-4-hydroxyproline (100 mol-%) in ethanol and acetyl chloride (120 mol-%). Dried ethanol is pre-cooled and stored in an ice/salt bath at 0° C., after which acetylchloride is added into the ethanol extreme slowly, during a 30 minute period. L-4-hydroxyproline is mixed with the dried ethanol, and it is then added into a HCl-ethanol solution. The mixture obtained is stirred at a refluxing temperature under argon. The obtained product is L-4-hydroxyproline ethylester hydrochloride salt.

L-4-hydroxyproline ethylester is prepared from L-4-hydroxyproline ethylester hydrochloride salt using an excess of an anionic ion exchange resin Amberlite IRA-400 (OH-form) in dried ethanol. The solvent is evaporated. L-4-hydroxyproline ethylester is obtained as a slightly viscous liquid.

Example 2

Functionalisation of an Amine Group of an Amino Acid with a (Meth)Acrylic Group

The esterified amino acid (100 mol-%, from Example 1) is dissolved in an organic solvent, such as in trifluoroethanol. The solution is cooled under argon flux to −10° C., and one equivalent of triethylamine as a base is added. The solution is then slowly heated to 0° C. and one equivalent of chloride of (meth)acrylic acid is added. The solution is further heated to room temperature (about 20-25° C.) and the reaction is allowed to continue during 24 hours. Thereafter, the solvents are evaporated and the crude product is purified by recrystallization or flash column chromatography.

Example 3

Functionalisation of a Carboxylic Group of an Amino Acid with a (Meth)Acrylic Group One equivalent of an amino acid is diluted and mixed into an organic solvent, e.g. in trifluoroethanol. An excess (e.g. ca. 2 eq) of (meth)acrylic acid anhydride is added into the mixture and the pH is adjusted to between 7.5 and 8 using 2 M NaOH solution. The reaction is allowed to proceed during about 24 hours at 5-10° C. The product is precipitated and washed employing an organic solvent, e.g. trifluoroethanol.

Example 4

Polyamide of an Amino Acid

A reaction flask is charged with the monomer from Example 1. The reaction system is equipped with a $N_2$(liquid)/acetone trap. Initially, the monomer is agitated during the first 5 minutes by flushing the system with nitrogen. The monomer is heated to 100° C., and the catalyst, calcium acetate (0.5 wt-%) is added. The reaction is heated further (to 150° C.) in high vacuum. By measuring viscosity throughout the reaction, the increase of molecular weight is monitored. At the end of the reaction, the product, polyamide of L-4-hydroxyproline, appeared to be hydrophilic.

Example 5

Functionalisation of a Polyamide Derivative of an Amino Acid with a (Meth)Acrylic Group A (meth)acrylic group is attached to the polyamide derivative of an amino acid (from Example 4) by diluting 100 mol-% of a polyamide in an organic solvent (e.g. in trifluoroethanol). The solution is cooled under argon flux to −10° C., and one equivalent of triethylamine is added. The solution is then slowly heated to 0° C. and one equivalent of chloride of (meth)acrylic acid is added. The solution is further heated to room temperature (about 20° C.) and the reaction is allowed to continue during 24 hours. Thereafter, the solvents are evaporated and the product is purified employing an organic solvent, e.g. trifluoroethanol. The final product is a viscous fluid.

Example 6

Polyester of an Amino Acid

The reaction solution from the preparation of L-4-hydroxyproline ethylester hydrochloride (from Example 1) is cooled to 30° C. 2 M of NaOH solution (100 mol-%) is added to the solution. After this, benzylchloride (100 mol-%) is added, and the obtained mixture is allowed to reflux for 1 hour. Then, 2 M of NaOH solution (100 mol-%) is added at ambient temperature (25° C.). The obtained L-4-N-benzyl-hydroxyproline ethylester (monomer) is a viscous liquid.

A reaction flask is charged with the purified monomer obtained. The reaction system is equipped with a $N_2$(liquid)/acetone trap. The monomer is heated to 150° C., and the catalyst, titanium isopropoxide (0.5 wt-%), is added. By measuring viscosity throughout the reaction, the increase of molecular weight is monitored. The obtained solid product is polyester of L-4-N-benzyl-hydroxyproline. An autoclave is charged with the polyester of L-4-N-benzyl-hydroxyproline, trifluoroethanol and palladium on charcoal (10%). The mixture is stirred at ambient temperature (25° C.) under hydrogen pressure (95 bar). At the end of the reaction, the catalyst is removed by filtration and the solvent evaporated. The obtained product is polyester of L-4-hydroxyproline.

Example 7

Functionalisation of a Polyester Derivative of L-4-Hydroxyproline with a (Meth)Acrylic Group A (meth)acrylic group is mixed with a polyester derivative of polyester of L-4-hydroxyproline (from Example 6) by diluting the polyester in trifluoroethanol. The solution is cooled under argon flux to −10° C., and an excess (2 eq) of (meth)acrylic acid anhydride is added and the pH is adjusted to basic with 2 M NaOH solution (pH 7.5-8). The reaction is allowed to continue during 24 hours at about 5-10° C. Thereafter, the product is precipitated and decanted. The solvents are evaporated and the product is washed employing an organic solvent (e.g. trifluoroethanol).

Example 8

Fully Degradable Hybrid Silica-Gel Particles

At ambient room temperature, tetraethoxysilane (TEOS), polyamide or polyester of L-4-hydroxyproline, deionized water, and hydrochloride acid are mixed in a mole ratio of TEOS, deionized water, and HCl: 500-600 eq, 1700-2000 eq, and 1 eq, respectively. The mole ratio of polyamide or polyester of L-4-hydroxyproline can vary between 1 and 600 eq compared to the amount of HCl. The sol solution is kept at 40° C. for polycondensation for 10-20 hours. The aged hybrid silica gel is dried at 50° C. for from 3 to 5 days. The solid hybrid material is ground and sieved to grain size 0.001<x<500 μm or cut to fibers (length from 0.5 to 5 mm, diameter from 10 to 500 μm).

Example 9

Partially Degradable Hybrid Silica-Gel Particles

At ambient room temperature, tetraethoxysilane (TEOS), deionized water, and hydrochloride acid are mixed in a mole ratio of TEOS, deionized water, and HCl: 500-600 eq, 1700-2000 eq, and 1 eq, respectively. The sol solution is kept at 40° C. for polycondensation for 10-20 hours. Then, 15 ml of this sol solution is mixed with 5 ml of a silane (e.g. 3-methacryloxypropyltrimethoxysilane, MPS), 5 ml of a dimethacrylate monomer (e.g. ethyleneglycol dimethacrylate, EGDMA), 0.1 g of camphorquinone (CQ) and 0.1 g of N,N-dimethylaminoethyl methacrylate (DMAEMA). The mixture is cured using UV-light by free radical polymerisation for 10 min. The solid hybrid material is ground and sieved to grain size 0.001<x<500 μm or cut to fibers (length from 0.5 to 5 mm, diameter from 10 to 500 μm).

Example 10

Manufacturing of nanofibers by Electrospinning

From Example 8 and 9, before the solid structure is formed and/or polymerised, the solution is employed as sol-gel precursors for fiber spinning. Additionally, the precursor solution can contain from 5 to 30 wt-% of a polymer, e.g. polyvinylalcohol (PVA) or carboxy methylcellulose (CMC). In order to produce nanofibers, the following parameters can be employed: needle diameter from 0.5 to 1.5 mm, flow rate from 0.1 to 0.3 ml/h, and from 10 to 20 kV of electrospinning voltage that is located at 15-30 cm from the needle tip. The solid hybrid material, i.e. nanofiber network, is ground and sieved to grain size 0.001<x<0.9 μm or cut to fibers (length from 0.5 to 5 mm, diameter from 0.001 to 1 μm). Alternatively, the obtained nanofibers are thermally treated at 300-700° C. before grounding.

Example 11

Manufacturing of a Sulfate Mineral Composite as a Filler Granule 50 wt-% of a monomer (e.g. MPS, EGDMA, bisphenol-A glycidyl methacrylate (BisGMA) or methylmethacrylate, MMA), is mixed with 50 wt-% of a sulfate mineral (e.g. CaSO4.2H2O). The mixture is polymerised (e.g. benzoylperoxide initiated and N,N-dimethyl-p-toluidine) for from 15 to 240 min. The solid hybrid material is ground and sieved to grain size of 0.001<x<500 μm.

Example 12

Coating of Particles and Manufacturing of a Filler Granule

From Examples 8, 9, and 10, the granules in the shape of particles or fibers are coated or preimpregated in a monomer resin or a solution that contains hydrolytic degradable polymer (e.g. polyester or polyamide of an amino acid, i.e. 50-1000 mg/ml, in an organic solvent, such as trifluoroethanol). The concentration is selected depending on the thickness of the coating aimed. In addition, the granules are naturally occurring, inorganic or organic fibers (e.g. E-glass fibers, cellulose fibers or collagen fibers). The solvent is evaporated from the granules leaving single granules that have a hydrolytically degradable outermost layer (with specific nanostructures) or sintered granules that are adhered to each other by hydrolytic degradable polymer.

Example 13

Manufacturing of a Filler Granule in Micrometer Scale (A)

In order to create the filler granules, the core of granules (e.g. E-glass fibers or spherical particles) are preimpregated in a monomer resin or solution that contains hydrolytic degradable polymer (50-1000 mg/ml). The concentration is selected depending on the thickness of the coating aimed. The particles are sintered with each other by evaporation of the preimpregnation solvent or by polymerising the monomer resin. The polymerisation is initiated with light, heat, ultrasound or other external energy source.

Example 14

Manufacturing of a Filler Granule in Micrometer Scale (B)

The filler granules are made having a core of bioactive glass, E-glass, an inorganic-organic hybrid structure, or sol-gel in different shapes and forms. Alternatively, the core granules are synthetic or natural polymer (e.g. polylactide acid, poly(caprolactone) or CMC). The core granules in the shape of particles or fibers are coated or preimpregated in a monomer resin or solution that contains hydrolytic degradable polymer (e.g. polyester or polyamide of an amino acid in an organic solvent, such as trifluoroethanol). Moreover, the preimpregnation monomer resin or solution contains other additives, such as an antibacterial agent (e.g. Gentamicin), a surface active agent, a therapeutically active agent, a growth factor, stem cells or other bioactive component. The particles are sintered with each other by evaporation of the preimpregnation solvent or by polymerisation of monomer resin. The polymerisation is initiated with light, heat, ultrasound or other external energy source. The solid hybrid granules is ground and sieved to grain size $0.001 < x < 0.9$ μm or cut to fibers (length from 0.5 to 5 mm, diameter from 0.001 to 1 μm).

Example 15

Manufacturing a Bulk Composite Comprising a Filler Granule

A commercial polymethylmethacrylate (PMMA) and polymethylmethacrylate-polymethylacrylate (PMMA-PMA) copolymer based bone cement (Palacos® R) is used. Each dose of surgical bone cement consists of 40 g of a PMMA-PMA copolymer and an ampoule with 18 g of methylmethacrylate (MMA) monomer. The mixture of PMMA-PMA/PMMA based bone cement with 10, 20, 30, 40, 50, 60, 70, or 80 wt-% of filler granules (from Examples 1-14) is employed for the preparation of a bulk composite. The polymer powder (PMMA-PMA copolymer) is first mixed with the filler granules for 5-10 min and then mixed with the monomer solution at room temperature. The monomer solution is a combination of MMA (50 wt-%), MPS (45 wt-%) and EGDMA (5 wt-%). The bone cement resin mixture is autopolymerised.

Example 16

In Vivo Curing of a Porous and Bioactive Bulk Composite as Synthetic Bone Graft A commercial polymethylmethacrylate (PMMA) and polymethylmethacrylate-palymethylacrylate (PMMA-PMA) copolymer based bone cement (Palacos® R) is used. Each dose of surgical bone cement consists of 40 g of a PMMA-PMA copolymer and an ampoule with 18 g of methylmethacrylate (MMA) monomer. The mixture of PMMA-PMA/PMMA based bone cement is used with 30 wt-% of pore-generating filler granule. For example, the filler granule is prepared from a derivative of L-4-hydroxyproline, polyamide or polyester of L-4-hydroxyproline (Examples 1-7) or their mixture. In addition, 10 wt-% of chopped silane treated E-glass fibres (length 2 mm, diameter 10 μm) that are preimpregnated in an organic solvent (e.g. a solution of 70 vol-% ethanol and 30 vol-% distilled water, optionally containing biodegradable polymer ca. 50-200 mg/ml). After evaporation of the solution, the filler granule contains some derivative of L-4-hydroxyproline as matrix. The liquid component of Palacos® R is modified using one or more methacrylic groups containing monomers (e.g. EDGMA, MPS, BisGMA). After 5-10 min mixing, the bulk composite material is implanted in the defect located in bone. The PMMA-based bone cement mixture is polymerised by benzoylperoxide initiated and N,N-dimethyl-p-toluidine catalysed autopolymerisation in 15 min. The composite becomes porous in the contact of body fluid.

Example 17

In Vivo Curing a Porous and Bioactive Bulk Composite as Synthetic Bone Graft A commercial PMMA and PMMA-PMA copolymer based bone cement (e.g. Palacos® R) is modified. The mixture of PMMA-PMA/PMMA based bone cement with 20 wt-% of bioactive glass granules and 10 wt-% of E-glass fibers are employed. The polymer powder is mixed with glass components and monomer solution at room temperature. The monomer solution is a combination of MMA (50 wt %), MPS (45 wt %) and EGDMA (5 wt %). The PMMA based bone cement mixture is polymerized by benzoylperoxide initiated and N,N-dimethyl-p-toluidine catalyzed autopolymerisation at room temperature. The composite becomes porous in the contact of body fluid.

Example 18

Ex Vivo Manufactured Porous and Bioactive Synthetic Bone Graft

In terms of residual monomers, methacrylate based monomers have a risk to cause an acute local toxicity. Typically, the content of residual monomer of PMMA based bone cements decreases to ca. 0.5% in 2-3 weeks. In fact, the PMMA based porous and bioactive bone cement composite according to this invention can be cured before the implantation. In addition, in order to avoid the use of autogenic bone grafts, ex vivo manufactured synthetic composite can be employed in the reconstruction of bone, like in the applications of computer-aided design osteotomy templates, the compression fractures of cancellous bone (e.g. osteochondral fractures, severe wrist fractures) or in the filling of bone cavities caused by tumors or infection.

The composite can be manufactured starting from a PMMA based bone cement (like Palacos® R). A mixture of the powder component of bone cement with 20, 30, 40, 50, 60, 70 wt-% of inorganic compound and reinforcing fibers (Examples 1-14) is employed for the preparation of porous and bioactive structure. The methacrylic compound-based resin is mixed with the inorganic components. The monomer solution is plain MMA or a combination of MMA (50 wt-%), MPS (45 wt-%) and EGDMA (5 wt-%). Alternatively, it is a combination of BisGMA (25 wt-%), MMA (25 wt-%), MPS (45 wt-%) and EGDMA (5 wt-%). The monomer mixture is polymerised by autopolymerisation, light or in an autoclave for from 15 to 240 min. The composite becomes porous in the contact of some solvent, e.g. after immersion in simulated body fluid (SBF) for from three days to five weeks at $(37\pm 1)°$ C.

Example 19

Ex Vivo Manufactured Porous and Bioactive Synthetic Bone Graft Bone Graft 20 ml of an epoxy resin (e.g. diglycidyl ether of bisphenol-A, DGEBA) is mixed with 3.8 ml of triethylenetetramine (TETA). 5 g of filler granules (from Example 1-14), 10 g of some sulfate mineral (e.g. $CaSO_4.2H_2O$), and 5 g of an inorganic substance (e.g. bioactive glass or chopped E-glass fibres) are mixed with the resin. The mixture is allowed to polymerize at room temperature. The composite becomes porous in the contact of a solvent.

The invention claimed is:
1. A filler granule consisting of:
a matrix component (1),
at least two base particles (2) that are at least mostly embedded in the matrix component (1), and
a fibrous component (3),
wherein the fibrous component (3) is attached to at least one of the base particles (2) and in that
a part of the fibrous component (3) protrudes out from the matrix component (1); and
at least a part of the filler granule is made of a material that is hydrophilically degradable, hydrolytically degradable, and/or enzymatically degradable;
wherein the size of the filler granule is 5 nm-200 µm;
wherein the matrix component (1) is a material selected from the group consisting of polylactides, polycaprolactones polydimethylmethacrylates, polyamides, polyesters of aminoacids, bisphenol-A glycidyl methacrylate, polyvinyl acetates, carboxy methyl celluloses, L-4-hydroxyproline ethylester, polyamide of L-4-hydroxyproline and mixtures thereof;
wherein the base particles (2) are made of a material selected from the group consisting of polylactides, polycaprolactones, polydimethylmethacrylates, polyamides, polyesters of amino acids, bisphenol A glycidyl methacrylate, polyvinyl acetates, carboxy methyl celluloses and mixtures thereof.
2. A filler granule according to the claim 1, characterised in that the fibrous component (3) is formed of fibres in the form of short fibres, continuous fibres, a fibre mat or a fibre web.
3. A filler granule according to the claim 1, characterised in that the fibrous component (3) is formed of fibres in the form of short fibres, continuous fibres, a fibre mat or a fibre web.
4. A filler granule according to the claim 2, characterised in that the diameter of the fibres is 1 nm-100 µm.

5. A filler granule according to the claim 1, characterised in that the fibrous component (3) is made of a material selected from the group consisting of E-glass, bioactive glasses, and mixtures thereof.
6. A filler granule according to the claim 1, characterised in that it comprises further reinforcing particles and/or fibres (4).
7. A method for manufacturing a filler granule consisting of:
a matrix component,
at least two base particles that are at least mostly embedded in the matrix component, and
a fibrous component that protrudes out from the matrix component,
wherein at least a part of the filler granule is made of a material that is hydrophilically degradable, hydrolytically degradable, and/or enzymatically degradable,
wherein the size of the filler granule is 5 nm-200 nm;
wherein the matrix component (1) is a material selected from the group consisting of polylactides, polycaprolactones, polydimethylmethacrylates, polyamides, polyesters of aminoacids, bisphenol-A glycidyl methacrylate, polyvinyl acetates, carboxy methyl celluloses, L-4-hydroxyproline ethylester, polyamide of L-4-hydroxyproline and mixtures thereof;
wherein the base particles (2) are made of a material selected from the group consisting of polylactides, polycaprolactones, polydimethylmethacrylates, polyamides, polyesters of amino acids, bisphenol A glycidyl methacrylate, polyvinyl acetates, carboxy methyl celluloses and mixtures thereof;
the method comprising the steps of:
mixing the fibrous component and the at least two base particles in such conditions that the fibrous component is attached to at least one of the base particles, and
mixing the thus obtained mixture with the matrix component or a precursor of the matrix component.
8. A method according to claim 7, characterised in that when a precursor of the matrix component is used, the method further comprises the curing of the precursor.
9. A method for forming a composite material, the method comprising the steps of:
providing a filler granule according to the claim 1; and
forming the composite using the filler granule.
10. A method for manufacturing a medical device, the method comprising the steps of:
providing a filler granule according to claim 1; and
forming a medical device at least partially comprising the filler granule.
11. A composite material comprising at least one filler granule according to the claim 1.
12. A filler granule consisting of:
a matrix component (1),
at least two base particles (2) that are at least mostly embedded in the matrix component (1), and
a fibrous component (3),
wherein the fibrous component (3) is attached to at least one of the base particles (2) and in that
a part of the fibrous component (3) protrudes out from the matrix component (1); and
at least a part of the filler granule is made of a material that is hydrophilically degradable, hydrolytically degradable, and/or enzymatically degradable;
wherein the size of the filler granule is 5 nm-200 µm;
wherein the matrix component (1) is a polydimethylmethacrylate;

wherein the base particles (2) are made of a polydimethyl-methacrylate.

\* \* \* \* \*